United States Patent
Zhao et al.

(10) Patent No.: US 6,534,574 B1
(45) Date of Patent: *Mar. 18, 2003

(54) HIGHLY NUCLEATED THERMOPLASTIC ARTICLES

(75) Inventors: Xiaodong Edward Zhao, Moore, SC (US); Darin L. Dotson, Spartanburg, SC (US); Brian G. Morin, Greer, SC (US); Brian M. Burkhart, Greenville, SC (US); Martin E. Cowan, Moore, SC (US); Jeffrey R. Jones, Inman, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/995,315

(22) Filed: Nov. 27, 2001

Related U.S. Application Data

(63) Continuation of application No. 09/815,832, filed on Mar. 24, 2001, now Pat. No. 6,465,551.

(51) Int. Cl.[7] .............................. C08K 5/09; C08K 5/10; C08K 5/12; C08K 5/13; C07C 69/74
(52) U.S. Cl. .................... 524/284; 524/285; 524/326; 524/367; 524/368; 524/396; 528/486; 560/120
(58) Field of Search ................................ 524/284, 285, 524/316, 317, 326, 367, 368; 528/486; 560/120

(56) References Cited

U.S. PATENT DOCUMENTS

| | | | |
|---|---|---|---|
| 3,207,735 A | 9/1965 | Wijga | 259/337 |
| 3,207,736 A | 9/1965 | Wijga | 259/337 |
| 3,207,737 A | 9/1965 | Wales | 160/303 |
| 3,207,738 A | 9/1965 | Wijga | 259/337 |
| 3,207,739 A | 9/1965 | Wales | 260/93.7 |
| 3,560,411 A * | 2/1971 | Ruyter et al. | |
| 3,686,361 A | 8/1972 | De Witt, III et al. | 260/873 |
| 4,016,118 A | 4/1977 | Hamada et al. | 260/17.4 |
| 4,314,039 A | 2/1982 | Kawai et al. | 525/1 |
| 4,371,645 A | 2/1983 | Mahaffey, Jr. | 524/108 |
| 4,442,025 A * | 4/1984 | Boelens et al. | |
| 4,463,113 A | 7/1984 | Nakagara et al. | 524/117 |
| 4,532,280 A | 7/1985 | Kobayashi et al. | 524/108 |
| 4,647,571 A | 3/1987 | Kolbo et al. | 514/475 |
| 4,843,061 A * | 6/1989 | Broekhof et al. | |
| 5,047,574 A | 9/1991 | Ohtani et al. | 560/120 |
| 5,049,605 A | 9/1991 | Rekers | 524/108 |
| 5,342,868 A | 8/1994 | Kimura et al. | 524/108 |
| 5,922,793 A | 7/1999 | Amos et al. | 524/159 |
| 5,929,146 A | 7/1999 | Amos et al. | 524/89 |
| 5,981,636 A | 11/1999 | Amos et al. | 524/108 |
| 6,096,851 A | 8/2000 | Amos et al. | 524/89 |

\* cited by examiner

*Primary Examiner*—Tae H. Yoon
(74) *Attorney, Agent, or Firm*—Terry T. Moyer; William S. Parks

(57) ABSTRACT

Compounds and compositions comprising specific metal salts of bicyclo[2.2.1]heptane dicarboxylate salts in order to provide highly desirable properties within polyolefin articles are provided. The inventive salts and derivatives thereof are useful as nucleating and/or clarifying agents for such polyolefin, provide excellent crystallization temperatures, stiffness, and calcium stearate compatibility within target polyolefin. Also, such compounds exhibit very low hygroscopicity and therefore excellent shelf stability as powdered or granular formulations. Polyolefin additive compositions and methods of producing polyolefin with such compounds are also contemplated within this invention.

17 Claims, 1 Drawing Sheet

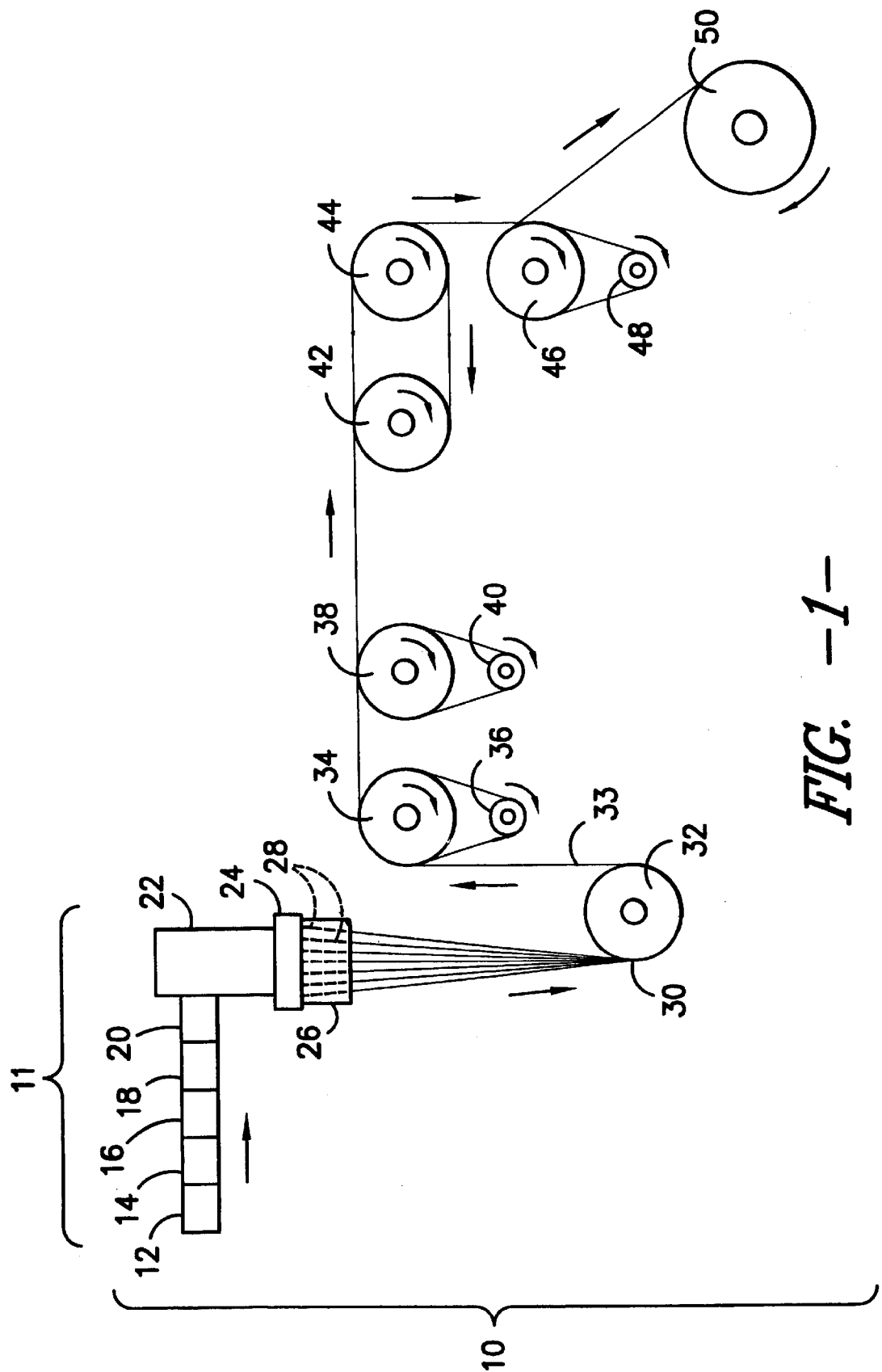
FIG. -1-

HIGHLY NUCLEATED THERMOPLASTIC ARTICLES

CROSS REFERENCE TO RELATED APPLICATIONS

This application is a continuation of application Ser. No. 09/815,832, filed on Mar. 24, 2001 now U.S. Pat. No. 6,465,551. This parent application is herein entirely incorporated by reference.

FIELD OF THE INVENTION

This invention relates to compounds and compositions comprising specific derivatives, such as diester salts, diacids, partial ester salts, and the like, of bicyclo[2.2.1] heptane in order to provide highly desirable properties within thermoplastic articles. The inventive salts and derivatives thereof are useful as nucleating and/or clarifying agents for such thermoplastics. Such compounds provide excellent crystallization temperatures, stiffness, and calcium stearate compatibility within target thermoplastics. Also, such compounds exhibit desirable migratory properties within thermoplastic articles and low hygroscopicity and therefore excellent shelf stability as powdered or granular formulations. Thermoplastic additive compositions and methods of producing thermoplastics with such compounds are also contemplated within this invention.

BACKGROUND OF THE PRIOR ART

All U.S. patents cited below are herein entirely incorporated by reference.

As used herein, the term "thermoplastic" is intended to mean a polymeric material that will melt upon exposure to sufficient heat but will retain its solidified state, but not prior shape without use of a mold or like article, upon sufficient cooling. Specifically, as well, such a term is intended solely to encompass polymers meeting such a broad definition that also exhibit either crystalline or semi-crystalline morphology upon cooling after melt-formation through the use of the aforementioned mold or like article. Particular types of polymers contemplated within such a definition include, without limitation, polyolefins (such as polyethylene, polypropylene, polybutylene, and any combination thereof), polyamides (such as nylon), polyurethanes, polyester (such as polyethylene terephthalate), and the like (as well as any combinations thereof).

Thermoplastics have been utilized in a variety of end-use applications, including storage containers, medical devices, food packages, plastic tubes and pipes, shelving units, and the like. More specific types of such thermoplastic end-uses, particularly those to which the inventive nucleating agent is contemplated as providing desirable nucleating effects therein, are listed below. Such base compositions, however, must exhibit certain physical characteristics in order to permit widespread use. Specifically within polyolefins, for example, uniformity in arrangement of crystals upon crystallization is a necessity to provide an effective, durable, and versatile polyolefin article. In order to achieve such desirable physical properties, it has been known that certain compounds and compositions provide nucleation sites for polyolefin crystal growth during molding or fabrication. Generally, compositions containing such nucleating compounds crystallize at a much faster rate than un-nucleated polyolefin. Such crystallization at higher temperatures results in reduced fabrication cycle times and a variety of improvements in physical properties, such as, as one example, stiffness.

Such compounds and compositions that provide faster and or higher polymer crystallization temperatures are thus popularly known as nucleators. Such compounds are, as their name suggests, utilized to provide nucleation sites for crystal growth during cooling of a thermoplastic molten formulation. Generally, the presence of such nucleation sites results in a larger number of smaller crystals. As a result of the smaller crystals formed therein, clarification of the target thermoplastic may also be achieved, although excellent clarity is not always a result. The more uniform, and preferably smaller, the crystal size, the less light is scattered. In such a manner, the clarity of the thermoplastic article itself can be improved. Thus, thermoplastic nucleator compounds are very important to the thermoplastic industry in order to provide enhanced clarity, physical properties and/or faster processing.

As an example of one type of nucleator, dibenzylidene sorbitol compounds are common nucleator compounds, particularly for polypropylene end products. Compounds such as 1,3-O-2,4-bis(3,4-dimethylbenzylidene) sorbitol (hereinafter DMDBS), available from Milliken Chemical under the trade name Millad® 3988, provide excellent nucleation characteristics for target polypropylenes and other polyolefins. Other well known compounds include sodium benzoate, sodium 2,2'-methylene-bis-(4,6-di-tert-butylphenyl) phosphate (from Asahi Denka Kogyo K.K., known as NA-11), talc, and the like. Such compounds all impart high polyolefin crystallization temperatures; however, each also exhibits its own drawback for large-scale industrial applications.

Other acetals of sorbitol and xylitol are typical nucleators for polyolefins and other thermoplastics as well. Dibenzylidene sorbitol (DBS) was first disclosed in U.S. Pat. No. 4,016,118 by Hamada, et al. as an effective nucleating and clarifying agents for polyolefin. Since then, large number of acetals of sorbitol and xylitol have been disclosed. Representative US patents include: Kawai, et al., U.S. Pat. No. 4,314,039 on di(alkylbenzylidene) sorbitols; Mahaffey, Jr., U.S. Pat. No. 4,371,645 on di-acetals of sorbitol having at least one chlorine or bromine substituent; Kobayashi, et al., U.S. Pat. No. 4,532,280 On di(methyl or ethyl substituted benzylidene) sorbitol; Rekers, U.S. Pat. No. 5,049,605 on bis(3,4-dialkylbenzylidene) sorbitols including substituents forming a carbocyclic ring.

Another example of the effective nucleating agents are the metal salts of organic acids. Wijga in U.S. Pat Nos. 3,207,735, 3,207,736, and 3,207,738, and Wales in U.S. Pat. Nos. 3,207,737 and 3,207,739, all patented Sep. 21, 1966, suggest that aliphatic, cycloaliphatic, and aromatic carboxylic, dicarboxylic or higher polycarboxylic acids, corresponding anhydrides and metal salts are effective nucleating agents for polyolefin. They further state that benzoic acid type compounds, in particular sodium benzoate, are the best embodiment of the nucleating agents.

Another class of nucleating agents, alluded to above, was suggested by Nakahara, et al. in U.S. Pat. No. 4,463,113, in which cyclic bis-phenol phosphates was disclosed as nucleating and clarifying agents for polyolefin resins. Kimura, et al. then suggests in U.S. Pat. No. 5,342,868 that the addition of an alkali metal carboxylate to basic polyvalent metal salt of cyclic organophosphoric ester can further improve the clarification effects of such additives. Compounds that are based upon this technologies are marketed under the trade name NA-11 and NA-21.

Furthermore, a certain class of bicyclic compounds, such as bicyclic dicarboxylic acid and salts, have been taught as polyolefin nucleating agents as well within Patent Cooperation Treaty Application WO 98/29494, to Minnesota Mining and Manufacturing. The best working example of this technology is embodied in disodium bicyclo[2.2.1]heptene dicarboxylate and formulations with such compounds.

Such compounds all impart relatively high polyolefin crystallization temperatures; however, each also exhibits its own drawback for large-scale industrial applications.

For example, of great interest is the compatibility of such compounds with different additives widely used within typical polyolefin (e.g., polypropylene, polyethylene, and the like) plastic articles. For instance, calcium stearate is a very popular acid neutralizer present within typical polypropylene formulations to protect the end product from catalyst residue attack. Unfortunately, most of the nucleator compounds noted above exhibit deleterious reactions with such compounds within polyolefin articles. For sodium, and other like metal ions, it appears that the calcium ion from the stearate transfers positions with the sodium ions of the nucleating agents, rendering the nucleating agents ineffective for their intended function. As a result, such compounds sometimes exhibit unwanted plate-out characteristics and overall reduced nucleation performance (as measured, for example) by a decrease in crystallization temperature during and after polyolefin processing. Other processing problems are evident with such compounds as well.

Other problems encountered with the standard nucleators noted above include inconsistent nucleation due to dispersion problems, resulting in stiffness and impact variation in the polyolefin article. Substantial uniformity in polyolefin production is highly desirable because it results in relatively uniform finished polyolefin articles. If the resultant article does not contain a well-dispersed nucleating agent, the entire article itself may suffer from a lack of rigidity and low impact strength.

Furthermore, storage stability of nucleator compounds and compositions is another potential problem with thermoplastic nucleators and thus is of enormous importance as well. Since nucleator compounds are generally provided in powder or granular form to the polyolefin manufacturer, and since uniform small particles of nucleating agents is imperative to provide the requisite uniform dispersion and performance, such compounds must remain as small particles through storage. Certain nucleators, such as sodium benzoate, exhibit high degrees of hygroscopicity such that the powders made therefrom hydrate easily resulting in particulate agglomeration. Such agglomerated particles may require further milling or other processing for deagglomeration in order to achieve the desired uniform dispersion within the target thermoplastic. Furthermore, such unwanted agglomeration due to hydration may also cause feeding and/or handling problems for the user.

Also of great interest is the compatibility of such compounds with different additives widely used within typical polyolefin (e.g., polypropylene, polyethylene, and the like) plastic articles. As noted previously, calcium stearate compatibility is particularly important. Unfortunately, most of the nucleators compounds noted above (such as sodium benzoate, NA-11, disodium bicyclo[2.2.1] heptene dicarboxylate) exhibit much deleterious nucleating efficacy with such compounds within polyolefin articles. In order to avoid combinations of these standard nucleators and calcium salts, other nonionic acid neutralizers, such as dihydrotalcite (DHT4-A), would be necessary for use in conjunction with such nucleators. Such a combination, however, has proven problematic in certain circumstances due to worsened aesthetic characteristics (e.g., higher haze), and certainly higher costs in comparison with standard calcium salts.

Some nucleating agents, such as certain DBS derivatives, exhibit certain practical deficiencies such as a tendency to plate-out at high processing temperatures. DBS derivatives, particularly where the aromatic rings are mono-substituted, show much improved thermal stability. However, such compounds also tend to exhibit undesirable migratory properties coupled with problematic organoleptic deficiencies within certain polyolefin articles. As a result, such compounds are limited in their practical in some important areas, such as medical device packaging.

These noticeable problems have thus created a long-felt need in the polyolefin nucleator compound industry to provide such compounds that do not exhibit the aforementioned problems and provide excellent peak crystallization temperatures for the target polyolefin themselves. To date, the best compounds for this purpose remain those noted above. Unfortunately, nucleators exhibiting exceptionally high peak crystallization temperatures, low hygroscopicity, excellent thermal stability, and non-migratory properties within certain target polyolefin, and compatibility with most standard polyolefin additives (such as, most importantly, calcium stearate) have not been accorded the polyolefin nucleator industry.

OBJECTS OF THE INVENTION

Therefore, an object of the invention is to provide a polyolefin nucleating agent that exhibit exceptional nucleation efficacy as indicated by exceptional high polymer peak crystallization temperatures within polyolefin articles. A further object of the invention is to provide a nucleating compound and compositions thereof that exhibit excellent calcium stearate compatibility within target polyolefin articles and formulations. Another objective of this invention is to provide formulations that exhibit extremely low hygroscopicity in order to accord an extremely good shelf-stable additive composition. Yet another object of this invention is to provide nucleating and clarifying compounds and compositions that exhibit exceptional thermal stability and non-migratory properties. Yet another object of the invention is to provide nucleating compounds that within the target polyolefin articles exhibit excellent mechanical properties. Additionally, it is an object of this invention to provide nucleating compounds or compositions that may be used in various polyolefin media for use in myriad end-uses.

Accordingly, this invention encompasses thermoplastic articles of different types comprising nucleating compounds that are preferably saturated metal or organic salts of bicyclic dicarboxylates, preferably, bicyclo[2.2.1]heptane-dicarboxylates, or, generally, compounds conforming to Formula (I)

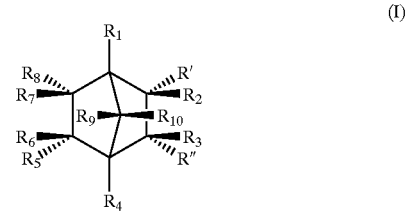

wherein $R_1$, $R_2$, $R_3$, $R_4$, $R_5$, $R_6$, $R_7$, $R_8$, $R_9$, and $R_{10}$ are individually selected from the consisting of hydrogen, $C_1$–$C_9$ alkyl, hydroxy, $C_1$–$C_9$ alkoxy, $C_1$–$C_9$alkyleneoxy, amine, and $C_1$–$C_9$ alkylamine, halogen, phenyl, alkylphenyl, and geminal or vicinal $C_1$–$C_9$ carbocyclic, R' and R" are the same or different and are individually selected from the group consisting of hydrogen, $C_1$–$C_{30}$ alkyl, hydroxy, amine, polyamine, polyoxyamine, $C_1$–$C_{30}$ alkylamine, phenyl, halogen, $C_1$–$C_{30}$ alkoxy, $C_1$–$C_{30}$ polyoxyalkyl, C(O)—$NR_{11}$C(O), and C(O)O—R''', wherein $R_{11}$ is selected from the group consisting of $C_1$–$C_{30}$ alkyl, hydrogen, $C_1$–$C_{30}$ alkoxy, and $C_1$–$C_{30}$ polyoxyalkyl, and wherein R''' is selected from the group consisting of hydrogen, a metal ion (such as, without limitation, $Na^+$, $K^+$, $Li^+$, $Ag^+$ and any other monovalent ions), an organic cation (such as ammonium as one non-limiting example), polyoxy-$C_2$–$C_{18}$-alkylene, $C_1$–$C_{30}$ alkyl, $C_1$–$C_{30}$ alkylene, $C_1$–$C_{30}$ alkyleneoxy, a steroid moiety (for example, cholesterol), phenyl, polyphenyl, $C_1$–$C_{30}$ alkylhalide, and $C_1$–$C_{30}$ alkylamine; wherein at least one of R' and R" is either C(O)-$NR_{11}$,C(O) or C(O)O—R''', wherein if both R' and R" are C(O)O-R'''then R'''both R' and R" may be combined into a single bivalent metal ion (such as $Ca^{2+}$, as one non-limiting example) or a single trivalent metal overbase (such as Al—OH, for one non-limiting example). Preferably, R' and R" are the same and R''' is either $Na^+$ or combined together for both R' and R" and $Ca^{2+}$. Other possible compounds are discussed in the preferred embodiment section below.

Preferably, as noted above, such a compound conforms to the structure of Formula

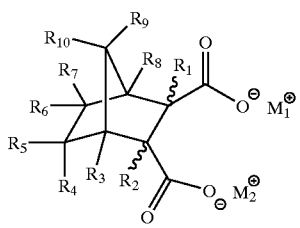

(I)

wherein $M_1$ and $M_2$ are the same or different and are independently selected from the group consisting of metal or organic cations or the two metal ions are unified into a single metal ion (bivalent, for instance, such as calcium, for example), and $R_1$, $R_2$, $R_3$, $R_4$, $R_5$, $R_6$, $R_7$, $R_8$, $R_9$ and $R_{10}$ are individually selected from the group consisting of hydrogen, $C_1$–$C_9$ alkyl, hydroxy, $C_1$–$C_9$ alkoxy, $C_1$–$C_9$ alkyleneoxy, amine, and $C_1$–$C_9$ alkylamine, halogen, phenyl, alkylphenyl, and geminal or vicinal $C_1$–$C_9$ carbocyclic. Preferably, the metal cations are selected from the group consisting of calcium, strontium, barium, magnesium, aluminum, silver, sodium, lithium, rubidium, potassium, and the like. Within that scope, group I and group II metal ions are generally preferred. Among the group I and II cations, sodium, potassium, calcium and strontium are preferred, wherein sodium and calcium are most preferred. Furthermore, the $M_1$ and $M_2$ groups may also be combined to form a single metal cation (such as calcium, strontium, barium, magnesium, aluminum, including monobasic aluminum, and the like). Although this invention encompasses all stereochemical configurations of such compounds, the cis configuration is preferred wherein cis-endo is the most preferred embodiment. The preferred embodiment polyolefin articles and additive compositions for polyolefin formulations comprising at least one of such compounds, broadly stated as saturated bicyclic carboxylate salts, are also encompassed within this invention.

DETAILED DESCRIPTION OF THE INVENTION

As noted above, in order to develop a proper polyolefin nucleator compound or composition for industrial applications, a number of important criteria needed to be met. The inventive nucleating agents meet all of these important requirements very well. For instance, as discussed in greater detail below, these inventive salts provide excellent high peak crystallization temperatures in a variety of polyolefin formulations, particularly within random copolymer polypropylene (hereinafter RCP) and homopolymer polypropylene (hereinafter HP). As a result, such inventive salts provide excellent mechanical properties for polyolefin articles without the need for extra fillers and rigidifying additives, and desirable processing characteristics such as improved (shorter) cycle time. The salts also show much improved hygroscopicity comparing to prior art and thus granular or powder formulations of such a salt do not agglomerate or clump together. Lastly, such inventive salts do not interact deleteriously with calcium stearate additives.

Such properties are highly unexpected and unpredictable, particularly in view of the closest prior art, the WO 98/29494 reference discloses nucleation and clarification additives for polyolefin articles including unsaturated [2.2.1] dicarboxylate salts; however, there is no exemplification of a saturated dicarboxylate salt of this type. The closest embodiment within that art is identified as disodium bicyclo[2.2.1] heptene dicarboxylate. After intensive investigations, it has been determined that, quite unexpectedly, as discussed below in greater detail, the hydrogenation of such compounds provides vastly improved nucleation efficacy for the inventive compounds and within the inventive polyolefin compositions. It has now been found that the saturation of Diels-Alder reaction products to form dicarboxylate salts, and in particular, without intending to limit the scope of the invention, saturated bicyclic dicarboxylate salts, provide unforeseen benefits for polyolefin nucleation processes.

As indicated in Table 1, below, the peak crystallization temperatures provided target polyolefin articles with these inventive saturated compounds are from about 2.5 to about 5° C. above that for the related unsaturated compounds. Such dramatic improvements are simply unexpected and are unpredictable from any known empirical or theoretical considerations. Furthermore, significant improvements in hygroscopicity of the saturated compounds were also unexpectedly observed. Such unpredictable improvements are of great practical significance as discussed before.

As noted above, the target formulations for introduction of such novel nucleating agents are thermoplastics, or more specifically, polyolefins. Such formulations may be utilized in myriad different end-uses, including without limitation, such broadly considered groups as fibers, thin film or thin-walled articles (e..g., pliable wrappers, thin-walled drinking cups, etc., having thicknesses between 0.1 and 15 mils, for example), thicker plaque or other like solid articles (e.g., from 15 to 150 mils in thickness), and even thicker-walled articles (e.g., greater than 150 mils thickness). Individual types of each group include, again, without limitation, either as complete articles, or as components of articles, the following:
  a) fibers: spun and nonwoven polyolefin, polyamide, polyaramid, and the like, fibers of any denier measurement, as well as blends with other synthetic or natural fibers (e.g., cotton, ramie, wool, and the like); b) thin film articles: cast films, candy wrappers, package wrappers (e.g., cigarette box wrappers, for example); and other like blown, extruded, or other similar type of film application, as well as thin-walled articles, such as drinking cups, thin containers, coverings, and the like;
  c) thicker plaque or other like solid articles: deli containers, water cups, cooler linings, syringes, labware, medical equipment, pipes, tubes, urinanalysis cups, intravenous bags, food storage containers, waste containers, cooler housings, automotive instrument panels, flower pots, planters, office storage articles, desk storage articles, disposable packaging (e.g., reheatable food containers, either thermoformed or thin-walled or high speed injection molded types), and the like; and d) even thicker-walled articles: i) automotive applications, such as door panels, instrument panels, body panels, fan covers, steering wheels, bumper fascia, fan shields, radiator shields, automotive fluid containers, battery cases, storage compartments, and the like; ii) large appliances, such as refrigerator linings, refrigerator parts (e.g., shelves, ice machine housings, door handles, and the like), dishwasher linings, dishwasher parts (e.g., racks, pipes, tubes, door handles, liquid and/or solid detergent storage compartments), washing machine drums, washing machine agitators, and the like; iii) small appliances, such as blender housings, blender containers, toaster oven housings, toaster oven handles, coffee pots, coffee pot housings, coffee pot handles, food processors, hair dryers, can openers, and the like; iv) housewares, such as large storage totes, large storage containers, lids for either such totes or containers, waste baskets, laundry baskets, shelves, coolers, and the like; v) consumer products, such as furniture (e.g., small chairs, tables, and the like), toys, sporting goods, disposable packaging (e.g., reheatable food containers), compact disc cases, DVD cases, CD-ROM cases, floppy disc containers, floppy disc housings, VHS tape cases, VHS tape housings, flower pots, planters, clothes hangers, lawn accessories (e.g., lawn tools, and the like), garden accessories (e.g., garden implements), lawn mower housings, fuel containers, pipes, tubes, hoses, tool boxes, tackle boxes, luggage, conduits, lawn trimmer housings, large trash cans, infant car seats, infant chairs (e.g., for dining tables), and the like.

Yet another surprise was the improved compatibility between these inventive saturated compounds and typical acid scavenger salt compounds utilized within polyolefin formulations and articles, such as calcium and lithium stearate. Such compatibility, coupled with the high peak crystallization temperatures available from the inventive compounds, thus provides a highly desirable thermoplastic nucelator compound. The inventive salts are thus added within the target polyolefin in an amount from about 50 ppm to about 20,000 pm by weight in order to provide the aforementioned beneficial characteristics, most preferably from about 200 to about 4000 ppm. Higher levels, e.g., 50% or more by weight, may also be used in a masterbatch formulation. Optional additives within the inventive salt-containing composition, or within the final polyolefin article made therewith, may include plasticizers, antistatic agents, stabilizers, ultraviolet absorbers, and other similar standard polyolefin thermoplastic additives. Other additives may also be present within this composition, most notably plasticizers, acid scavengers, antimicrobials (preferably silver-based ion-exchange compounds, such as ALPHASAN® antimicrobials available from Milliken & Company), antioxidants, flame retardants, light stabilizers, antistatic agents, colorants, pigments, perfumes, chlorine scavengers, and the like.

The term polyolefin or polyolefin resin is intended to encompass any materials comprised of at least one polyolefin compound. Preferred examples include isotactic and syndiotactic polypropylene, polyethylene, poly(4-methyl) pentene, polybutylene, and any blends or copolymers thereof, whether high or low density in composition. The polyolefin polymers of the present invention may include aliphatic polyolefins and copolymers made from at least one aliphatic olefin and one or more ethylenically unsaturated co-monomers. Generally, the co-monomers, if present, will be provided in a minor amount, e.g., about 10 percent or less or even about 5 percent or less, based upon the weight of the polyolefin (e.g. random copolymer polypropylene), but copolymers containing up to 25% or more of the co-monomer (e.g., impact copolymers) are also envisaged. Other polymers or rubber (such as EPDM or EPR) may also be compounded with the polyolefin to obtain the aforementioned characteristics. Such co-monomers may serve to assist in clarity improvement of the polyolefin, or they may function to improve other properties of the polymer. Other examples include acrylic acid and vinyl acetate, etc. Examples of olefin polymers whose transparency can be improved conveniently according to the present invention are polymers and copolymers of aliphatic monoolefins containing 2 to about 6 carbon atoms which have an average molecular weight of from about 10,000 to about 2,000,000, preferably from about 30,000 to about 300,000, such as, without limitation, polyethylene, linear low density polyethylene, isotactic polypropylene, syndiotactic polypropylene, crystalline ethylenepropylene copolymer, poly(1-butene), polymethylpentene, 1-hexene, 1-octene, and vinyl cyclohexane. The polyolefins of the present invention may be described as basically linear, regular polymers that may optionally contain side chains such as are found, for instance, in conventional low density polyethylene.

Although polyolefins are preferred, the nucleating agents of the present invention are not restricted to polyolefins, and may also give beneficial nucleation properties to polyesters such as polyethylene terephthalate (PET), polybutylene terephthalate (PBT), and polyethylene naphthalate (PEN), as well as polyamides such as Nylon 6, Nylon 6,6, and others. Generally, any thermoplastic composition having some crystalline content may be improved with the nucleating agents of the present invention.

The compositions of the present invention may be obtained by adding the inventive saturated bicyclic dicarboxylic salt (or combination of salts or composition comprising such salts) to the thermoplastic polymer or copolymer and merely mixing the resultant composition by any suitable means. Alternatively, a concentrate containing as much as about 20 percent by weight of the inventive saturated [2.2.1] salt in a polyolefin masterbatch comprising the required acid scavenger may be prepared and be subsequently mixed with the target resin. Furthermore, the inventive compositions (with other additives potentially) may be present in any type of standard thermoplastic (e.g., polyolefin, most preferably) additive form, including, without limitation, powder, prill, agglomerate, liquid suspension, and the like, particularly comprising dispersion aids such as polyolefin (e.g., polyethylene) waxes, stearate esters of glycerin, montan waxes, mineral oil, and the like. Basically, any form may be exhibited by such a combination or composition including such combination made from blending, agglomeration, compaction, and/or extrusion.

The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

BRIEF DESCRIPTION OF THE DRAWINGS

The accompanying drawings, which are incorporated in and constitute a part of this specification, illustrate a potentially preferred embodiment of producing inventive fiber and/or yarn thermoplastic articles in accordance with this invention and together with the description serve to explain the principles of the invention as it concerns such fibers wherein:

FIG. 1 is a schematic of the potentially preferred method of producing low-shrink polypropylene.

DETAILED DESCRIPTION OF THE DRAWING AND OF THE PREFERRED EMBODIMENT

FIG. 1 depicts the non-limiting preferred procedure followed in producing the inventive low-shrink polypropylene fibers. The entire fiber production assembly 10 comprises an extruder 11 comprising four different zones 12, 14, 16, 18 through which the polymer (not illustrated) passes at different, increasing temperatures. The molten polymer is mixed with the nucleator compound (also molten) within a mixer zone 20. Basically, the polymer (not illustrated) is introduced within the fiber production assembly 10, in particular within the extruder 11. The temperatures, as noted above, of the individual extruder zones 12, 14, 16, 18 and the mixing zone 20 are as follows: first extruder zone 12 at 205° C., second extruder zone 14 at 215° C., third extruder zone 16 at 225° C., fourth extruder zone 18 at 235° C., and mixing zone 20 at 245° C. The molten polymer (not illustrated) then moves into a spin head area 22 set at a temperature of 250° C. which is then moved into the spinneret 24 (also set at a temperature of 250° C.) for strand extrusion. The fibrous strands 28 then pass through a heated shroud 26 having an exposure temperature of 180° C. The speed at which the polymer strands (not illustrated) pass through the extruder 11, spin pack 22, and spinneret 24 is relatively slow until the fibrous strands 28 are pulled through by the draw rolls 32, 34, 38. The fibrous strands 28 extend in length due to a greater pulling speed in excess of the initial extrusion speed within the extruder 11. The fibrous strands 28 are thus collected after such extension by a take-up roll 32 (set at a speed of 370 meters per minute) into a larger bundle 30 which is drawn by the aforementioned draw rolls 34, 38 into a single yarn 33. The draw rolls are heated to a very low level as follows: first draw roll ÷68° C. and second draw roll ÷88° C., as compared with the remaining areas of high temperature exposure as well as comparative fiber drawing processes. The first draw roll 34 rotates at a speed of about 377 meters per minute and is able to hold fifteen wraps of the polypropylene fiber 33 through the utilization of a casting angle between the draw roll 34 and the idle roll 36. The second draw roll 38 rotates at a higher speed of about 785 meters per minute and holds eight wraps of fiber 33, and thus requires its own idle roll 40. After drawing by these cold temperature rolls 34, 38, the fiber is then heat-set by a combination of two different heat-set rolls 42, 44 configured in a return scheme such that eighteen wraps of fiber 33 are permitted to reside on the rolls 42, 44 at any one time. The time of such heat-setting is very low due to a low amount of time in contact with either of the actual rolls 42, 44, so a total time of about 0.5 seconds is standard. The temperatures of such rolls 42, 44 are varied below to determine the best overall temperature selection for such a purpose. The speed of the combination of rolls 42, 44 is about 1290 meters per minute. The fiber 33 then moves to a relax roll 46 holding up to eight wraps of fiber 33 and thus also having its own feed roll 48. The speed of the relax roll 46 is lower than the heat-set roll (1280 meters per minute) in order to release some tension on the heat-set fiber 33. From there, the fiber 33 moves to a winder 50 and is placed on a spool (not illustrated).

Preferred Embodiments of the Invention

This invention can be further elucidated through the following examples where examples of particularly preferred embodiment within the scope of the present invention are presented.

Production of Inventive Salts

EXAMPLE 1

Disodium bicyclo[2. 2.1]heptane-2,3-dicarboxylate

To a solution of disodium bicyclo[2.2.1]hept-5-ene-2,3-dicarboxylate (10.0 g, from example 3) in water (100 g) was added 0.5 g palladium on activated carbon (5 wt %). The mixture was transferred into a Parr reactor and was subjected to hydrogenation (50 psi, room temperature) for 8 hours. The activated carbon was filtered out, and the water was removed in vacuo at 75 ° C. The resulting product was dried and milled (m.p >300 ° C. ). NMR and IR analyses were consistent with that of the expected structure.

EXAMPLE 2

Calcium bicyclo[2.2.1]heptane-2,3-dicarboxylate

To a solution of disodium bicyclo[2.2.1]heptane-2,3-dicarboxylate (22.6 g, 0.1 mols) in water (150 g) was added a solution of calcium chloride dihydrate (14.7 g, 0.1 mols) in water (100 g). The mixture was stirred at 60° C. for 2 hours. The resulting white precipitate was filtered. The white powdery product was dried and milled (m.p. >300° C. ).

Other Group I and II salts, lithium, potassium, rubidium, magnesium, strontium, and barium salts of bicyclo[2.2.1] heptane dicarboxylates were synthesized through similar procedures of reacting a Group I or II salt with disodium bicyclo[2.2.1]heptane-2,3-dicarboxylate.

EXAMPLE 3

Hydrogen Sodium bicyclo[2.2.1]heptane-2,3-dicarboxylate 80.0 g (487.3 mmoles) of himic anhydride (164.16 g/mole) and 175 ml of water was charged into a 1L round bottom flask with stirring. To this solution was added 19.69 g (492.3 mmoles) of NaOH (40.00 g/mol). The solution was stirred with heat until all components were in solution. Upon cooling, crystals began to form and 500 ml of water was added to fully solubilize all solids. Palladium on activated carbon (5 wt %) was added to the aqueous solution. The mixture was transferred into a Parr reactor and was subjected to hydrogenation (50 psi, room temperature) for 8 hours. The activated carbon was filtered out, and the water was removed in vacuo at 75° C. The resulting product was dried and milled (m.p >300 C). An IR analysis was consistent with that of the expected structure. GS-MS showed >99% saturation of the double bond.

EXAMPLE 4

Hydrogen Lithium/Sodium bicyclo[2. 2.1]heptane-2, 3-dicarboxylate (Half Neutralized)

82.0 g (500.0 mmoles) of himic anhydride (164.16 g/mole) and 175 ml of water was charged into a 1L round bottom flask with stirring. To this solution was added 10.00 g (250.0 mmoles) of NaOH (40.00 g/mol) and 5.99 g (250.0 mmoles) of LiOH (23.95 g/mol). The solution was stirred with heat until all components were in solution. Half of this solution was transferred to another 1L round bottom flask. Upon cooling, palladium on activated carbon (5 wt %) was added to the remaining aqueous solution. The mixture was transferred into a Parr reactor and was subjected to hydrogenation (50 psi, room temperature) for 8 hours. The activated carbon was filtered out, and the water was removed in vacuo at 75° C. The resulting product was dried and milled (m.p >300° C). An IR analysis was consistent with that of the expected structure. GS-MS showed >99% saturation of the double bond.

EXAMPLE 5

Hydrogen Lithium/Sodium bicyclo[2.2.1]heptane-2,3-dicarboxylate (Three Quarters Neutralized)

The other half of the solution of Hydrogen Lithium/Sodium bicyclo[2.2.1]heptane-2,3-dicarboxylate (half neutralized) solution was further neutralized with an additional 5.00 g (125.0 mmoles) of NaOH (40.00 g/mol) and 2.99 g (125.0 mmoles) of LiOH (23.95 g/mol). Upon cooling, palladium on activated carbon (5 wt %) was added to the aqueous solution. The mixture was transferred into a Parr reactor and was subjected to hydrogenation (50 psi, room temperature) for 8 hours. The activated carbon was filtered out, and the water was removed in vacuo at 75° C. The resulting product was dried and milled (m.p >300° C.). An IR analysis was consistent with that of the expected structure. GS-MS showed >99% saturation of the double bond.

EXAMPLE 6

Lithium/Sodium bicyclo[2.2.1]heptane-2,3-dicarboxylate 82.0 g (500.0 mmoles) of himic anhydride (164.16 g/mole) and 175 ml of water was charged into a 1L round bottom flask with stirring. To this solution was added 10.00 g (250.0 mmoles) of NaOH (40.00 g/mol) and 5.99 g (250.0 mmoles) of LiOH (23.95 g/mol). The solution was stirred with heat until all components were in solution. Half of this solution was transferred to another 1L round bottom flask, and an additional 5.00 g (125.0 mmoles) of NaOH (40.00 g/mol) and 2.99 g (125.0 mmoles) of LiOH (23.95 g/mol) was added to the remaining solution. Upon cooling, palladium on activated carbon (5 wt %) was added to the aqueous solution. The mixture was transferred into a Parr reactor and was subjected to hydrogenation (50 psi, room temperature) for 8 hours. The activated carbon was filtered out, and the water was removed in vacuo at 75° C. The resulting product was dried and milled (m.p >300° C.). An IR analysis was consistent with that of the expected structure. GS-MS showed >99% saturation of the double bond.

EXAMPLE 7

Bicyclo[2.2.1]heptane-2,3-dicarboxylic acid 100.0 g (438.3 mmoles) of disodium bicyclo[2.2.1]heptane-2,3-dicarboxylate (228.15 g/mole) and 280 ml of water was charged into a 2L Erlenmeyer flask with stirring. To this solution was added fuming sulfuric acid until the pH of the resulting solution was ~1. As the pH became acidic, a white flocculent precipitate formed. The solution was stirred and cooled to room temperature. The precipitate was removed by vacuum filtration and dried overnight in a vacuum oven at 110° C. The resulting product was dried and milled. An IR analysis was consistent with that of the expected structure.

EXAMPLE 8

Sodium; 2-octadecyloxycarbonyl-3-bicyclo[2.2.1]heptanecarboxylate 50.0 g (301 mmoles) of bicyclo[2.2.1]heptane-2,3-dicarboxyl anhydride (166.17 g/mole) and 81.2 g (300 mmoles) of stearyl alcohol (270.49 g/mol) were charged into a 500 mL round bottom flask with stirring assembly, thermometer, and Dean-Stark condenser. The solution was stirred with heat for two hours at 150° C. to yield 125 g of the acid-ester, 2-octadecyloxycarbonyl -3-bicyclo[2.2.1]heptanecarboxylic acid as confirmed by IR and acid number. 50.0 g (114.6 mmoles) of this acid-ester product was stirred with 500 ml methanol in a 600 ml beaker until the solution turned milky. The suspension was brought to a pH of 11.5 by dropwise addition of NaOH (4 g/40 ml methanol). Methanol was removed by rotary evaporation and the resulting sample was air dried at room temperature. An IR analysis was consistent with that of the expected structure.

EXAMPLE 9

Sodium; 2-(poly(propyleneoxide-monobutylether))ylcarbonyl-3-bicyclo [2.2.]heptanecarboxylate 20.0 g (120 mmoles) of bicyclo[2.2.1]heptane-2,3-dicarboxyl anhydride (166.17 g/mole) and 40.9 g (120 mmoles) of stearyl alcohol (340 g/mol) were charged into a 200 mL round bottom flask with stirring assembly, thermometer, and an argon blanket. The solution was stirred with heat for two hours at 150° C. to yield the acid-ester as a liquid as confirmed by IR and acid number. The liquid was transferred to a 250 ml beaker with 100 ml of methanol and brought to a pH of 12 by dropwise addition of NaOH (4 g/40 ml methanol). Methanol was removed by rotary evaporation and the resulting sample was air dried at room temperature. An IR analysis was consistent with that of the expected structure.

EXAMPLE 10

2-cholesterylcarbonyl-3-bicyclo[2.2.I]heptanecarboxylic acid 8.59 g (51.7 mmoles) of bicyclo[2.2.1]heptane-2,3-dicarboxyl anhydride (166.17 g/mole) and 20 g (51.7 mmoles) of cholesterol (386.66 g/mol) were charged into a 100 mL round bottom flask with stirring assembly and thermometer. The solution was stirred with heat for two hours at 150° C. to yield the acid-ester as confirmed by IR and acid number. The resulting sample was air dried at room temperature. An IR analysis was consistent with that of the expected structure.

EXAMPLE 11 (Comparative)

Disodium bicyclo[2.2.I]hept-5-ene-2,3-dicarboxylate

To a suspension of endo-bicyclo[2.2.1]hept-5-ene-2,3-dicarboxylic acid (16.4 g, 0.1 mols) in water (100 g) was added sodium hydroxide (8.0 g, 0.2 mols) at room temperature. The mixture was then stirred at 80° C. for 2 hours. A clear, homogeneous solution was obtained. Water was removed in vacuum at 75° C. and the resulting white crystalline product was dried and milled (m.p. >300° C. ).

Other comparative examples of commercial samples of Millad® 3988, sodium benzoate, NA-11, and NA-21 were used in this evaluation as well.

Nucleation Efficacy Test

Thermoplastic compositions (plaques) were produced comprising the additives from the Examples above and sample homopolymer polypropylene (HP) resin plaques, produced dry blended in a Welex mixer at ~2000 rpm, extruded through a single screw extruder at 400–450° F., and pelletized. Accordingly, one kilogram batches of target polypropylene were produced in accordance with the following table

| HOMOPOLYMER POLYPROPYLENE COMPOSITION TABLE | |
|---|---|
| Component | Amount |
| Polypropylene homopolymer (Himont Profax ® 6301) | 1000 g |
| Irganox ® 1010, Primary Antioxidant (from Ciba) | 500 ppm |
| Irgafos ® 168, Secondary Antioxidant (from Ciba) | 1000 ppm |
| Calcium Stearate, Acid Scavenger | 800 ppm |
| Inventive Nucleator | as noted |

The same composition but with Himont Profax® 6501 polypropylene homopolymer present instead was also utilized for the preferred embodiments. The base HP (either 6301 or 6501) and all additives were weighed and then blended in a Welex mixer for 1 minute at about 1600 rpm. All samples were then melt compounded on a Killion single screw extruder at a ramped temperature from about 204° to 232° C. through four heating zones. The melt temperature upon exit of the extruder die was about 246° C. The screw had a diameter of 2.54 cm and a length/diameter ratio of 24:1. Upon melting the molten polymer was filtered through a 60 mesh (250 micron) screen. Plaques of the target polypropylene were then made through extrusion into an Arburg 25 ton injection molder. The molder molder was set at a temperature anywhere between 190 and 260° C, with a range of 190 to 240° C. preferred, most preferably from about 200 to 230° C. The plaques had dimensions of about 51 mm×76 mm×1.27 mm, and the mold had a mirror finish which was transferred to the individual plaques. The mold cooling circulating water was controlled at a temperature of about 25° C.

Testing for nucleating effects and other important criteria were accomplished through the formation of plaques of clarified polypropylene thermoplastic resin. These plaques were formed through the process outlined above with the specific compositions listed above in the above Table.

These plaque formulations are, of course, merely preferred embodiments of the inventive article and method and are not intended to limit the scope of this invention. The resultant plaques were then tested for peak crystallization temperatures (by Differential Scanning Calorimetry). Crystallization is important in order to determine the time needed to form a solid article from the molten polyolefin composition. Generally, a polyolefin such as polypropylene has a crystallization temperature of about 110° C. at a cooling rate of 20° C./min. In order to reduce the amount of time needed to form the final product, as well as to provide the most effective nucleation for the polyolefin, the best nucleator compound added will invariably also provide the highest crystallization temperature for the final polyolefin product. The nucleation composition efficacy, particular polymer peak crystallization temperature ($T_c$), was evaluated by using DSC according to ASTM D-794-85. To measure these temperatures, the specific polypropylene composition was heated from 60° C. to 220° C. at a rate of 20° C. per minute to produce a molten formulation and held at the peak temperature for 2 minutes. At that time, the temperature was then lowered at a rate of 20° C. per minute until it reached the starting temperature of 60° C. The crystallization temperature was thus measured as the peak maximum during the crystallization exotherm. The clarification performance of the nucleators was measured using ASTM D 1003–92.

The following Table lists the peak crystallization temperatures for the plaques prepared above (with 6301 PP denoting Himont Profax® 6301 as the polypropylene and 6501 PP denoting Himont Profax®b 6501 as the polypropylene):

EXPERIMENTAL TABLE 1

Performance of Bicyclic Nucleators in Polypropylene Homopolymer

| Additives | Additive Conc. (%) | Polym. Cryst. Temp | % Haze |
|---|---|---|---|
| Example 1 (in 6301 PP) | 0.1 | 126 | 34% |
| Example 1 (in 6301 PP) | 0.25 | 128 | 30% |
| Example 2 (in 6301 PP) | 0.1 | 125 | 48% |
| Example 2 (in 6301 PP) | 0.25 | 127 | 45% |
| Example 3 (in 6501 PP) | 0.2 | 124.9 | 38.5% |
| Example 4 (in 6301 PP) | 0.1 | 125.5 | 44.9% |
| Example 6 (in 6501 PP) | 0.2 | 126.1 | 35.8% |
| Example 7 (in 6501 PP) | 0.25 | 122.9 | 41.7% |
| Example 8 (in 6301 PP) | 0.25 | 126.3 | 37.2% |
| Example 9 (in 6301 PP) | 0.25 | 126 | 32.1% |
| Example 10 (in 6501 PP) | 0.25 | 119.3 | 61.1% |
| Lithium bicyclo [2.2.1]heptane dicarboxylate (in 6301 PP) | 0.25 | 123 | 56% |
| Potassium bicyclo[2.2.1]heptane dicarboxylate (in 6301 PP) | 0.25 | 125 | 67% |
| Rubidium bicyclo[2.2.1]heptane dicarboxylate (in 6301 PP) | 0.25 | 123 | 55% |
| Magnesium bicyclo[2.2.1]heptane dicarboxylate (in 6301 PP) | 0.25 | 117 | 78% |
| Barium bicyclo[2.2.1]heptane dicarboxylate (in 6301 PP) | 0.25 | 121 | 71% |
| Strontium bicyclo[2.2.1]heptane dicarboxylate (in 6301 PP) | 0.25 | 124 | 56% |
| None (in 6301 PP) | | 110 | 68% |
| Example 11 (Comparative) (in 6301 PP) | 0.1 | 122 | 50% |
| Example 11 (Comparative) (in 6301 PP) | 0.25 | 123 | 46% |
| DMDBS (in 6301 PP) | 0.25 | 123 | 11% |
| Na-11 (in 6301 PP) | 0.1 | 124 | 32% |
| Na-21 (in 6301 PP) | 0.25 | 123 | 20% |

The data shows that the inventive products exhibit significantly higher polymer peak crystallization temperature and, in some instances, lower haze than the comparative unsaturated compound.

Another important test for nucleation efficacy is the crystallization half-time (T½). This measurement was conducted on DSC where the specific polypropylene composition was heated from 60° C. to 220° C. at a rate of 20° C. per minute to produce a molten formulation and held at the peak temperature for 2 minutes. At that time, the temperature was then lowered quickly to 140° C., where the sample was held. The exotherm of crystallization was measured with time. The time where exactly one-half of the heat of crystallization is generated was recorded as the crystallization half time. Shorter crystallization half time is indicative of higher nucleation efficacy. In a practical sense, a shorter crystallization half time is an indicator of a shorter cycle time, and thus of significant value.

EXPERIMENTAL TABLE 2

| Crystallization Half Time in Homopolymer Additives | Loading (%) | T1/2 (minutes) |
|---|---|---|
| Example 11 | 0.25 | 4.50 |
| Example 1 | 0.25 | 0.98 |
| Example 2 | 0.25 | 1.40 |

The data shows that the inventive compounds in Example 1 and Example 2 exhibit significantly shorter crystallization half time.

Calcium Stearate Compatibility Test

In this test, the nucleators were tested in formulations with and without calcium stearate. The nucleation efficacy of the nucleators in each formulation was studied by measuring polymer crystallization temperature. The formulations and testing conditions are identical with those discussed above. A drop of 2° C. or more is considered a failure.

EXPERIMENTAL TABLE 3

Calcium Stearate Compatibility Test

| Additives | Loading (%) | Loading of CaSt (%) | Polym. Peak Crys. Temp. (C) |
|---|---|---|---|
| Example 2 | 0.25 | 0 | 128 |
| Example 2 | 0.25 | 0.08 | 128 |
| Example 11 | 0.25 | 0 | 127 |
| Example 11 | 0.25 | 0.08 | 127 |
| NA-11 | 0.1 | 0.08 | 124 |
| NA-11 | 0.1 | 0.08 | 121 |
| Example 1 | 0.25 | 0 | 123 |
| Example 1 | 0.25 | 0.08 | 121 |

The data shows that only the inventive nucleators in Example 1 and Example 2 pass the compatibility test with calcium stearate.

Hygroscopicity Test

These tests were carried out on the milled products to give adequate surface area for moisture uptake. Two grams of each example were spread out on a watch glass and weighed immediately after drying in a vacuum oven. The samples were then placed in a controlled humidity (65%) environment and the weight was taken each day for 7 days. The percent weight gain was defined as the percent moisture uptake. Table 5 below summarizes the results:

EXPERIMENTAL TABLE 4

Hygroscopicity Test Data

| Entry | Sample | Weight Gain (% w/w) |
|---|---|---|
| 1 | Example 11 | 8% |
| 2 | Example 1 | 1% |
| 3 | Example 2 | 0% |

It is clear from the above data that saturation of Example 3 reduces the hygroscopicity over that of the prior art significantly, and the use of calcium as the metal reduces the moisture uptake to zero.

Nucleation Efficacy in Polyester

The inventive additives were also tested as nucleating agents for polyester. Additives were compounded with a C.W. Brabender Torque Rheometer at 5000 ppm into Shell Cleartuff™ 8006 PET bottle grade resin having an IV of 0.80. All resin was dried to less than 20 ppm water. Samples were taken, pressed, and rapidly cooled into 20–40 mil films. All samples were dried at 150° C. under vacuum for 6 h prior to analysis. The samples were analyzed under nitrogen on a Perkin Elmer System 7 differential scanning calorimeter using a heating and cooling rate of 20° C./min. The polymer peak crystallization temperature was measured as described before. The data is shown in Table 6 below:

EXPERIMENTAL TABLE 5

Polyester Nucleating Results

| Sample | Peak Cryst. Temp. (° C.) |
|---|---|
| Control | 155 |
| Example 11 | 184 |
| Example 1 | 194 |

Thus, the inventive saturated compound exhibited much improved nucleation of polyester over the control with no nucleator compound and the unsaturated nucleator compound.

End-Use Applications for the Inventive Nucleating Agents a) Fibers

Yarn Production

Yarn was made by compounding Amoco 7550 fiber grade polypropylene resin (melt flow of 18) with a nucleator additive and a standard polymer stabilization package consisting of 500 ppm of Irganoxg® 1010, 1000 ppm of Irgafos® 168 (both antioxidants available from Ciba), and 800 ppm of calcium stearate. The base mixture was compounded at 2500 ppm in a twin screw extruder (at 220° C. in all zones) and made into pellets. The additive was Example 1, above, and was compared with a control with no additive.

The pellets were then fed into the extruder on an Alex James & Associates fiber extrusion line as noted above in FIG. 1. Yarn was spun with the extrusion line conditions shown in Table 1 using a 68 hole spinneret, giving a yarn of nominally 150 denier. For each additive, four yarns were spun with heat-set temperatures of 100°, 110°, 120°, and 130° C. respectively. These temperatures are the set temperatures for the controller for the rolls 42, 44. In practice, a variation is found to exist over the surface of the rolls 42, 44, up to as much as 10° C. Pellets with no nucleator additive were used to make control fibers.

The measurements below have a statistical error of +/−0.4 percentage units.

The yarns were tested for shrinkage in hot air at 150° C. and 130° C. by marking a 10" section of yarn, placing it in an oven for five minutes at the measurement temperature, and similarly measuring the % shrinkage after removing the yarn from the oven. Again, five samples were measured, and the average shrinkage results are reported for each sample in Table 1. The shrink measurements are listed below the tested nucleators for each yarn sample. The yarn samples were as follows:

| POLYPROPYLENE YARN COMPOSITION TABLE Yarn Samples with Specific Nucleators Added | |
|---|---|
| Yarn Sample | Nucleator Added |
| A | from Example 1, above |
| B (Comparative) | None (control) |

Fiber and Yarn Physical Analyses

These sample yarns were then tested for shrink characteristics with a number of different variables including heat-set temperatures differences (on the heat-set rolls) during manufacture and different heat-exposure conditions (hot air at various temperatures and boiling water exposure at temperatures in excess of 100° C.). The results are tabulated below:

| FIBER EXPERIMENTAL TABLE Experimental Shrink Measurements for Sample Yarns | | | |
|---|---|---|---|
| Sample Yarn | Heatset Temp. (° C.) | Shrinkage Test and Temp., (° C.) | Shrinkage |
| A | 110 | 150 Hot air | 16% |
| A | 120 | 150 Hot air | 13% |
| A | 130 | 150 Hot air | 13.5% |
| A | 140 | 150 Hot air | 7.5% |
| A | 110 | 130 Hot air | 9.4% |
| A | 120 | 130 Hot air | 8% |
| A | 130 | 130 Hot air | 6.2% |
| A | 140 | 130 Hot air | 4.0% |
| B | 110 | 150 Hot air | 19.9% |
| B | 120 | 150 Hot air | 18.2% |
| B | 130 | 150 Hot air | 15% |
| B | 140 | 150 Hot air | 10% |
| B | 110 | 130 Hot air | 12.2% |
| B | 120 | 130 Hot air | 10.3 |
| B | 130 | 130 Hot air | 8.4% |
| B | 140 | 130 Hot air | 4.0% |

The inventive fibers were also tested for tenacity and modulus strength comparisons to the control. In each instance (differing only in relation to heatset temperatures), the inventive fibers were comparable to those measured for the control fibers and yarns. Thus, the addition of the inventive compounds within the target polypropylene fibers provided excellent improved physical properties.

b) Thin Film or Thin-Walled Articles

Thermoforming of Thin-walled Drinking Cups

Produced were 8.5 g drinking cups having dimensions of: height—139 mm, top diameter—93 mm, thickness—0.2 mm (8 mils), and Volume—560 ml.

The sample cups were made from low melt flow polypropylene homopolymer (MFR=4)(Exxon non-nucleated Escorene PP 7035E7 Medium Impact Copolymer base powder) with sheet extrusion conducted using a Mirex-W Reifenhauser sheet extruder equipped with a coat-hanger manifold sheet die. The Mirex-W had a 3 roll, 410-mm (16.1 in) diameter upstack. The roll width was 900 mm (35.4 in). The sheet extruder was run in-line with an Illig RDM 54K thermoformer including a former oven having longitudinal row control for the upper and lower infrared ceramic heaters. The mold was polished aluminum and used a Delrin plug-assist. The melt temperature for all the samples was approximately 237° C. The temperature of the lower roll was 60° C., the middle was 80° C., and the upper was also 60° C. Cycle time was determined for each sample as noted below by increasing the line speed until parts could not be feed to the stacker (e.g., the cup wall had not cooled sufficiently to withstand the loading force of the stacker).

| Trial Result Table of Maximum Number Of Cycles with Commercial and Experimental Nucleating Agents | | | | | | | | |
|---|---|---|---|---|---|---|---|---|
| | Control | 1200 ppm DMDBS | 1200 ppm NA-21 | 800 ppm NA-11 | 400 ppm from Ex. 1, above | 800 ppm from Ex. 1, above | 500/ 1200 ppm from Ex. 1, above | 500/ 1500 ppm DMDBS/ Ex. 1 |
| Max Cycle Time (cycles/ minutes) | 17.2 | 24.7 | 27.6 | 26.4 | 28.5 | 29.1 | 30.3 | 30.3 |

The data show that the inventive compounds provide (and thus the inventive thin-walled or thin film articles exhibit) significant cycle time improvement comparing to the un-nucleated control and resins containing other commercial nucleating agents.

c) Thicker Plaque or Other Like Articles (Having Thicknesses Between About 15 and 150 mils)

Injected Molded Container

A rectangular container comprising polypropylene having dimensions of 170×115×70 mm, wall thickness of 0.5 mm (about 20 mils) and volume of approximately 1 liter was produced having a weight of 23–24 g. The container was produced through the utilization of a Husky S90 Thin Wall Injection Mould (TWIM) Machine, highly polished, and equipped with cooling system so that the mould temperature can be regulated between 10–60° C. The mold also had an ejector system that allows molded part to be removed from the mold rapidly without damage. The material used was a homopolymer PP (as noted above) exhibiting a melt flow rate of from 40–45 g/10 min. The articles were made easily with the same formulations as noted above (6301 PP; about 2000 ppm of Example 1 added) and exhibited suitable resiliency as a small container for foodstuffs, and the like.

d) Thicker-Walled Articles Having Thicknesses Greater than 150 mils

Injection Molded Domed Lids for Medium Sized Tote

The part made measured 15×22 in and weighed 565 g and having a white color (due to metering white pigment into the feed hopper)(thickness of about 160–170 mils) and comprised Exxon non-nucleated Escorene PP 7035E7 Medium Impact Copolymer base powder (MFR=4). The part was molded on a 1000-ton Cincinnati Milacron Injection Molding Machine with a 2-cavity mold. A typical injection molding process is used to make the part:

The temperature of the barrel is controlled between 240–255° C. and die temperature of 300° C. This produced a polymer melt of approximately 220–240° C. The mold temperature was controlled at 30–40° C. The shot weight used was 60 mm. The injection speed of 425 mm/s and injection pressure of 2200 psi was used. The entire cycle time used to make a good part from injection to part ejected was 4 seconds. Different parts were made from unnucleated resin, inventive resin, and other resins comprising the aforementioned commercial nucleators.

Table of Cycle Time with Commercial and Experimental Nucleating Agents

|  | Control | DMDBS | NA-11 | Ex. 1 |
|---|---|---|---|---|
| Total Cycle time(s) | 26.2 | 20.8 | 22.6 | 20.0 |

The data show that the inventive nucleating agent provides significant cycle time improvement comparing to the un-nucleated control and resins containing commercial nucleating agents.

Furthermore, flexural modulus was measured as well for these samples, as noted in the following table:

Table of Flexural Modulus with Various Nucleating Agents

|  | Control | NA-11 | Ex. 1 |
|---|---|---|---|
| Flex Modulus (MPa) | 1057 | 1266 | 1277 |

The data show the inventive nucleating agent provides significant improvement and/or comparable physical property enhancements.

Hamper Lid

A Colormatrix Liquid Platinum color was metered into the feed hopper and the same polypropylene formulation as above for the tote lid (Exxon non-nucleated Escorene PP 7035E7 Medium Impact Copolymer base powder) was mixed therewith and molded on a 550 ton Cincinnati Milacron Injection Molding Machine with a single cavity mold. The five samples run in this trial were visc-broken from a MFR=4 to a MFR=35 during compounding. A typical injection molding process was used to make the part wherein the temperature of the barrel was controlled between 240–255° C. and the die temperature was about 300° C. These conditions produced a polymer melt of approximately 220–240° C. The mold temperature was controlled at 30–40° C. and the shot weight used was 60 mm. An injection speed of 425 mm/s and an injection pressure of 2200 psi were used. The entire cycle time used to make a good part from injection to part ejected was 4 seconds.

Trial Result
Table of cycle Time with Commercial and Experimental Nucleating Agents

|  | Control | Sodium benzoate | NA-11 | Ex. 1 |
|---|---|---|---|---|
| Total Cycle time(s) | 9.0 | 7.0 | 6.5 | 5.5 |

The data show that the inventive nucleating compound provides significant cycle time improvement comparing to the un-nucleated control and resins containing commercial nucleating agent.

Table of Flexural Modulus with Various Nucleating Agents

|  | Control | Ex. 1 |
|---|---|---|
| Flex Modulus (MPa) | 1122 | 1275 |

The data show the inventive nucleating agent provides significant improvement in physical property enhancement for such thick thermoplastic parts.

Having described the invention in detail it is obvious that one skilled in the art will be able to make variations and modifications thereto without departing from the scope of the present invention. Accordingly, the scope of the present invention should be determined only by the claims appended hereto.

That which is claimed is:

1. A thermoplastic article selected from the group consisting of a fiber, a thin film or thin-walled article, a thicker plaque or other solid article having a thickness between about 15 and 150 mils, and a thicker-walled article having a thickness greater than 150 mils, wherein said thermoplastic article comprises a compound conforming to the structure of Formula (I)

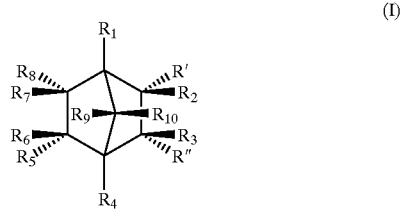

wherein $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxy, $C_1$–$C_9$ alkoxy, $C_1$–$C_9$ alkyleneoxy, amine, and $C_1$–$C_9$ alkylamine, halogen, phenyl, alkylphenyl, and geminal or vicinal carbocyclic having up to 9 carbon atoms; R' and R" are the same or different and are individually selected from the group consisting of hydrogen, $C_1$–$C_{30}$ alkyl, hydroxy, amine, polyamine, polyoxyamine, $C_1$–$C_{30}$ alkylamine, phenyl, halogen, $C_1$–$C_{30}$ alkoxy, $C_1$–$C_{30}$ polyoxyalkyl, C(O)—$NR_{11}$ C(O)O—R''',and C(O)O—R''', wherein $R_{11}$ is selected from the group consisting of $C_1$–$C_{30}$ alkyl, hydrogen, $C_1$–$C_{30}$ alkoxy, and $C_1$–$C_{30}$ polyoxyalkyl; wherein each R''' of both R' and R" may be the same or different and are individually selected from the group consisting of hydrogen, a monovalent cation, polyoxy-$C_2$–$C_{18}$-alkylene, $C_1$–$C_{30}$ alkylene, $C_1$–$C_{30}$ alkylene, $C_1$–$C_{30}$ alkyleneoxy, a steroid moiety, phenyl, polyphenyl, $C_1$–$C_9$ alkylhalide, and $C_1$–$C_9$ alkylamine, or wherein each R''' of both R' and R" may be combined to form a moiety selected from the group consisting of a single bivalent metal cation and a single trivalent metal overbase; wherein at least one of R' and R" is selected from the group consisting of C(O)—$NR_{11}$ C(O)O—R''' and C(O)O—R''', wherein if a C(O)—$NR_{11}$ C(O)O—R''' group is present, then R''' for that group is selected from the group consisting of hydrogen, a monovalent cation, or wherein if another a C(O)—$NR_{11}$ C(O)O—R''' group is present, then the R''' of both groups may be combined to form a single bivalent metal cation.

2. The thermoplastic article of claim 1 wherein said compound conforms to the structure of Formula (II)

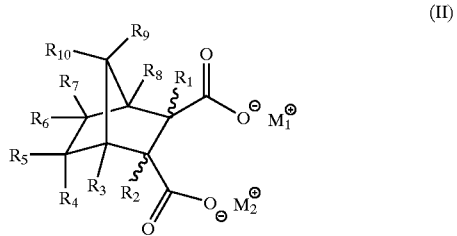

wherein $M_1$ and $M_2$ are the same or different, such that $M_1$ and $M_2$ may individually constitute monovalent cations, or $M_1$ and $M_2$ may be combined to form a single multivalent cation; wherein $M_1$ and $M_2$ are independently selected from the group consisting of at least one metal cation and at least one organic cation, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxy, $C_1$–$C_9$ alkoxy, $C_1$–$C_9$ alkyleneoxy, amine, $C_1$–$C_9$ alkylamine, halogen, phenyl, alkylphenyl, and geminal or vicinal $C_1$–$C_9$ carbocyclic.

3. The thermoplastic article of claim 2 wherein said at least one metal cation is present and is selected from the group consisting of Group I and Group II metal ions.

4. The thermoplastic article of claim 3 wherein $M_1$ and $M_2$ are the same monovalent cation selected from the group consisting of sodium, potassium, lithium, rubidium, and silver.

5. The thermoplastic article of claim 3 wherein $M_1$ and $M_2$ are combined into a single multivalent cation selected from the group consisting of magnesium, calcium, strontium, barium, zinc, and aluminum.

6. The thermoplastic article of claim 4 wherein $M_1$ and $M_2$ are both sodium.

7. The thermoplastic article of claim 5 wherein said single moiety is calcium.

8. The thermoplastic article of claim 1 comprising a polyolefin.

9. The thermoplastic article of claim 2 comprising a polyolefin.

10. The thermoplastic article of claim 3 comprising a polyolefin.

11. The thermoplastic article of claim 4 comprising a polyolefin.

12. The thermoplastic article of claim 5 comprising a polyolefin.

13. The thermoplastic article of claim 6 comprising a polyolefin.

14. The thermoplastic article of claim 8 wherein said article is a fiber.

15. The thermoplastic article of claim 8 wherein said article is a thin film article.

16. The thermoplastic article of claim 8 wherein said article is a thicker plaque or other solid article having a thickness between about 15 and 150 mils.

17. The thermoplastic article of claim 8 wherein said article is a thicker-walled article having a thickness greater than 150 mils.

* * * * *

UNITED STATES PATENT AND TRADEMARK OFFICE
CERTIFICATE OF CORRECTION

PATENT NO. : 6,534,574 B1
DATED : March 18, 2003
INVENTOR(S) : Ed Zhao et al.

It is certified that error appears in the above-identified patent and that said Letters Patent is hereby corrected as shown below:

Column 21,
Line 29, delete "$C_1$-$C_9$" and insert -- $C_1$-$C_{30}$ --, and delete "$C_1$-$C_9$" and insert -- $C_1$-$C_{30}$ --.

Signed and Sealed this

Twenty-third Day of September, 2003

JAMES E. ROGAN
*Director of the United States Patent and Trademark Office*